United States Patent
Ward et al.

(10) Patent No.: US 9,132,629 B2
(45) Date of Patent: Sep. 15, 2015

(54) METHOD OF DETECTING DROPS

(75) Inventors: Kenneth Ward, Corvallis, OR (US); Alexander Govyadinov, Corvallis, OR (US)

(73) Assignee: HEWLETT-PACKARD DEVELOPMENT COMPANY, L.P., Houston, TX (US)

(*) Notice: Subject to any disclaimer, the term of this patent is extended or adjusted under 35 U.S.C. 154(b) by 349 days.

(21) Appl. No.: 13/123,804

(22) PCT Filed: Oct. 15, 2008

(86) PCT No.: PCT/US2008/011809
§ 371 (c)(1),
(2), (4) Date: Apr. 12, 2011

(87) PCT Pub. No.: WO2010/044765
PCT Pub. Date: Apr. 22, 2010

(65) Prior Publication Data
US 2011/0221815 A1    Sep. 15, 2011

(51) Int. Cl.
*B41J 29/38* (2006.01)
*B41J 2/045* (2006.01)
*B41J 2/21* (2006.01)
*G01N 35/10* (2006.01)

(52) U.S. Cl.
CPC ............ *B41J 2/04581* (2013.01); *B41J 2/0451* (2013.01); *B41J 2/0458* (2013.01); *B41J 2/04561* (2013.01); *B41J 2/2142* (2013.01); *G01N 35/1016* (2013.01); *G01N 2035/1034* (2013.01)

(58) Field of Classification Search
None
See application file for complete search history.

(56) References Cited

U.S. PATENT DOCUMENTS

| | | | |
|---|---|---|---|
| 4,779,003 | A | 10/1988 | Tatsuno |
| 5,646,654 | A | 7/1997 | Widder |
| 6,576,155 | B1 | 6/2003 | Barbera-Guillem |
| 6,744,046 | B2 | 6/2004 | Valaskovic |
| 6,958,482 | B2 | 10/2005 | Martinez et al. |
| 7,483,767 | B2 | 1/2009 | Montaser et al. |
| 8,333,453 | B2 * | 12/2012 | Dudenhoefer et al. ......... 347/19 |
| 2002/0140760 | A1 | 10/2002 | Bruch et al. |
| 2002/0158938 | A1 | 10/2002 | Doval |
| 2003/0090534 | A1 | 5/2003 | Valero et al. |
| 2004/0233465 | A1 | 11/2004 | Coyle et al. |
| 2006/0044341 | A1 | 3/2006 | Reichelsheimer et al. |

(Continued)

FOREIGN PATENT DOCUMENTS

| | | |
|---|---|---|
| JP | 2004058627 | 2/2004 |
| KR | 20050092985 A | 9/2005 |

OTHER PUBLICATIONS

International Searching Authority, "International Preliminary Report on Patentability", issued in connection with PCT Application No. PCT/US2008/011809, Apr. 19, 2011, 5 pages.

(Continued)

*Primary Examiner* — Geoffrey Mruk
*Assistant Examiner* — Bradley Thies
(74) *Attorney, Agent, or Firm* — Ingrid McTaggart

(57) ABSTRACT

A liquid dispensing device (10), including a drop ejection device (12) including an orifice (18) adapted for ejecting drops therefrom, a single detection device (28) positioned to receive drop information from the ejected drops of the drop ejection device, and a controller (40) that receives the drop information and uses the drop information to determine a number of drops ejected from the drop ejection device.

13 Claims, 1 Drawing Sheet

(56) References Cited

U.S. PATENT DOCUMENTS

| | | | |
|---|---|---|---|
| 2006/0172060 | A1 | 8/2006 | Teichman et al. |
| 2006/0261295 | A1 | 11/2006 | Barea |
| 2007/0023037 | A1 | 2/2007 | Larsen |
| 2007/0024658 | A1 | 2/2007 | Diol |
| 2008/0018909 | A1 | 1/2008 | Osaka |
| 2008/0186373 | A1 | 8/2008 | Rolly |
| 2008/0259107 | A1* | 10/2008 | Farr et al. .................... 347/14 |
| 2009/0015609 | A1 | 1/2009 | Choo |
| 2009/0086190 | A1 | 4/2009 | Kodama et al. |
| 2009/0231403 | A1 | 9/2009 | Shi et al. |
| 2009/0244163 | A1 | 10/2009 | Govyadinov |
| 2009/0288580 | A1 | 11/2009 | Cai |
| 2010/0033519 | A1 | 2/2010 | Cai et al. |
| 2011/0109679 | A1 | 5/2011 | Govyadinov et al. |
| 2011/0121021 | A1* | 5/2011 | Dudenhoefer et al. ........... 222/1 |
| 2014/0098156 | A1 | 4/2014 | Taff et al. |

OTHER PUBLICATIONS

International Searching Authority, "International Search Report", issued in connection with PCT Application No. PCT/US2008/011809, mailed on May 29, 2009, 2 pages.

International Searching Authority, "Written Opinion", issued in connection with PCT Application No. PCT/US2008/011809, mailed on May 29, 2009, 4 pages.

United States Patent and Trademark Office, "Final Office Action", issued in connection with U.S. Appl. No. 14/123,194, mailed on Dec. 16, 2014, 20 pages.

United States Patent and Trademark Office, "Office Action", issued in connection with U.S. Appl. No. 14/123,194, mailed on Jun. 20, 2014, 15 pages.

International Searching Authority, "International Preliminary Report on Patentability", issued in connection with PCT Application No. PCT/US2011/038608, Dec. 2, 2013, 5 pages.

International Searching Authority, "International Search Report and Written Opinion", issued in connection with PCT Application No. PCT/US2011/038608, mailed on Feb. 17, 2012, 7 pages.

Particle Sciences, Inc., "Manufacture of Microspheres as Carrier Particles for Active Biomolecules", Technical Paper, accessed on Feb. 10, 2015 [http://www.particlesciences.com/docs/Manufacture_of_Microspheres_as_Carrier_Particles_for_Active_Biomolecules.pdf], 3 pages.

United States Patent and Trademark Office, "Office Action", issued in connection with U.S. Appl. No. 14/588,821, mailed on Apr. 1, 2015, 20 pages.

United States Patent and Trademark Office, "Notice of Allowance", issued in connection with U.S. Appl. No. 14/123,194, mailed on May 11, 2015, 27 pages.

* cited by examiner

Fig. 2 FOR A TOTAL INTENDED VOLUME OF 1000pL

| DROP VOLUME (pL) | 18 | 21 | 25 | 29 |
|---|---|---|---|---|
| TOTAL NUMBER DROPS | 56 | 48 | 40 | 34 |

METHOD OF DETECTING DROPS

BACKGROUND

Liquid dispensing devices, such as thermal ink jet printers, may be utilized to dispense precise and minute amounts of liquid, such as droplets of liquid, into individual wells of a multiple-well tray, such as in pharmaceutical testing, for example. Precise numbers of drops should be dispensed into the individual wells in order to ensure accurate test results. There is a need, therefore, to detect the number of drops dispensed from a liquid dispensing device. Moreover, there is a need for detecting the presence of drops from a liquid dispensing device to determine if the orifices of the device are functioning.

BRIEF DESCRIPTION OF THE DRAWINGS

FIG. 2 is a table showing a correlation between the intended total volume and the total number of drops to achieve the intended total volume for a particular drop volume.

DETAILED DESCRIPTION OF THE DRAWINGS

Figure 1:
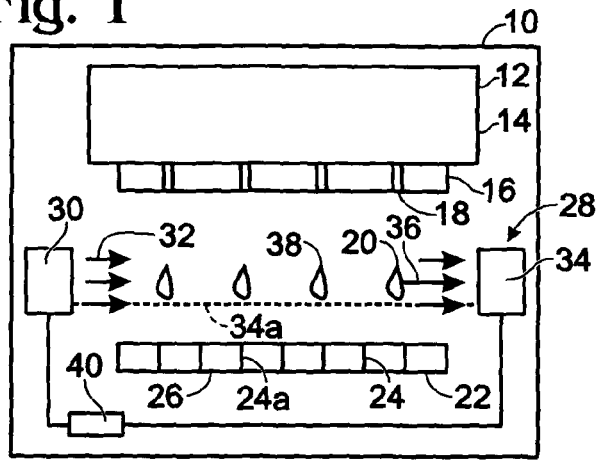
FIG. 1 is a schematic side cross-sectional view of one example embodiment of a liquid dispensing device.

FIG. 1 is a schematic side cross-sectional view of one example embodiment of a liquid dispensing device 10, which in the embodiment shown may include a drop ejection device 12. Drop ejection device 12 may be a printing or an imaging device, and in the example embodiment shown, may be a thermal ink jet device. Drop ejection device 12 may include a printhead or multiple printheads 14 that may each include an orifice layer 16, such as an orifice plate, for example, including multiple orifices 18 therein for ejecting fluid 20 therefrom. Drop ejection device 12 may be one of a thermal ejection device, and a piezo ejection device, for example.

Orifice layer 16 may include one or several orifices 18 or may include thousands of orifices 18, as may be suited for a particular application. Fluid 20 may be any fluid as desired for a particular liquid dispensing application. The drop ejection device 12 generates droplets 38 of fluid 20 of differing drop volumes depending on fluid 20 and construction details of device 12. In the field of pharmaceutical testing, fluid 20 may primarily be any water-miscible organic solvent, such as dimethyl sulfoxide (DMSO), for example. In other embodiments, fluid 20 may be primarily water, methanol, isopropanol, ethanol, glycerol, acetone, pyridine, tetrahydrofuran, acetonitrile, and dimethylformamide, for example.

Liquid dispensing device 10 may be utilized to dispense precise and minute amounts of liquid into a liquid receiving device 22, such as into individual wells 24 of a multiple-well tray 26, as used in pharmaceutical testing, for example. In some example embodiments liquid receiving device 22 may be a biochemical testing device, a diagnostic strip device, or a device to receive a coating, for example. Precise volume amounts should be dispensed into the individual wells 24 in order to ensure accurate test results. There is a need, therefore, to increase the reliability and/or predictability of the volume of fluid 20, such as the predictability of the number of drops 38, dispensed into each of the individual wells 24.

Liquid dispensing device 10 may include a drop detection device 28. The drop detection device may be chosen from one of an electrostatic detection device, a capacitive detection device, an acoustic drop detection device, and an optical detection device, for example. In the embodiment shown, drop detection device 28 may include a light emitting device 30 that emits a light 32, such as a laser, and a single light detecting device 34 positioned with respect to orifice layer 16 such that light detecting device 34 receives light 36 reflected, scattered or otherwise emanating from drops 38 of fluid 20 ejected from orifice 18 and illuminated by light 32. Light detecting device 34 may be a photodetector chosen from one of a photo diode, a CMOS, a charge-coupled device, a photo multiplying tube, and any other photodetector. Light emitting device 30 may be chosen from one of a laser, a light emitting diode, an arc discharge lamp, and any other high intensity light source.

Light detecting device 34 may be connected to a controller 40 that may use the light information received from light 36 by detecting device 34, so as to determine the number of drops ejected into, or to be ejected into, each compartment of liquid receiving device 22, such as into each of the individual wells 24 of a well tray 26, with each well 24 receiving different intended volumes, as one example.

Controller 40 may include a database of information such as electronically or otherwise stored formulas, graphs, tables, and the like that correlate different types of information, such as a correlation of drop volume for individual drops for a variety of fluid solutions, for example. Controller 40 may also include a means for determining the number of drops 38 of particular volume that are required for an intended dispense volume into an individual well 24. In the embodiment shown, drop detection device 28 is a light based detection device. However, drop detection device 28 may be an electrostatic device, a capacitive device, an acoustic device, a magnetic detection device, an optical device, or any other drop detection device that will function for a particular application.

In one example embodiment, drop detection device 28 may be a light scattering drop detector including a light emitting device 30, with a 1 millimeter (mm) laser beam waist (the critical dimension in a drop's trajectory direction). Light detecting device 34 may be a single channel photocell or a photocell array that is capable of detecting up to 5,000 to 8,000 drop-events per second at a nominal drop velocity >10 m/s, which is typical for both thermal and piezo-ink jet technologies. Using a 0.1 mm laser beam waist, the same detector may be capable of detecting up to 50,000 to 80,000 drop-events per second at the same drop ejecting conditions. As the drops 38 fall, light 32 from laser diode 30 illuminates the drop 38, and light 36 scattered from the drops is detected by photo cell 34. At a drop velocity at 10 m/second, the expected time-of-flight (TOF) of the drops is 10 micro seconds (μsec). The single channel light detection device 34 may be positioned at a single, predetermined angle 34a relative to the direction of incident light 32 from laser diode 30. Accordingly, angle 34a is shown as the angle between incident light 32 and scattered light 36. In the embodiment shown in FIG. 1, angle 34a is near 0°, i.e., device 34 is positioned almost in line with the path of light 32 from light emitting device 30. At angle of 0° a shadow effect by obscuring light by the drop will occur. The device will detect scattering light from near 0° up to 180°, which corresponds to complete back scattering/retro reflection. For typical inkjet drop sizes >10 μm a diffraction is significant at low angles (close to 0°) and may have a significant contribution at higher angles only for small particles and long light wavelengths such as when the particle size is comparable and even smaller than the wavelength. In one preferred embodiment, an angle of 10-45° is utilized for light scattering. In general, angles of 10-90 degrees are readily useable, with large signals closer to 0 degrees, although there is a decrease of light intensity at exactly zero degrees because of superposition of the shadow effect and low angular diffraction contributions. Accordingly, an angle 34a of 20 degrees for particular implementation may be desirable.

In one embodiment the drops 38 may continue to fall into a drop collection reservoir (not shown) for later use in liquid dispensing device 10, such that the fluid is not wasted, or drops 38 may fall into a separate reservoir (not shown) to be collected for disposal. However, in the embodiment shown the drops 38 fall directly into a predetermined individual well, such as a well 24a, for example, of well tray 26 and real time processing is conducted to determine the exact number of drops to be dispensed into the particular well 24a so that well 24a will contain a minute, precise, predetermined and known volume of fluid 20.

In a simple embodiment, light emitting device 30 may be a laser diode or a light emitting diode (LED) and light detecting device 34 may be a single photodiode, which may be interfaced via a preamplifier to a pulse counter on a single personal computer or a controller device such as an FPGA or PLC for example. In more sophisticated implementations, a peak detector may be used to measure a value of the amplitude signal, which will be used for number of drops evaluation as well (see FIG. 3). This versatile system could be used to count drops that are being generated up to 100 KHz and accomplish the counting in real time, as opposed to offline precalibration methods such as optical or gravimetric methods currently utilized. Accordingly, the current device provides extremely rapid feedback to the dispense system. Moreover, because every drop is counted, the precision and accuracy of the disclosed method is better than gravimetric or optical methods currently in use. Furthermore, use of a single light detection device 34, positioned at a single angle 34a with respect to light emitting device 30, greatly simplifies the device operation and lowers the cost of device 1, and greatly simplifies the mathematical calculations that may be conducted by controller 40 in determining a drop count of drops 38 from printhead 14.

In another embodiment, drop detection device 28 may be utilized to determine a health of individual ones of orifices 18 of orifice layer 16. In particular, drop detection device 28 may be utilized to determine the presence or absence of a drop ejected from a particular orifice of multiple orifices 18. The absence of a drop ejected from a particular orifice when a drop is attempted to be ejected from that orifice, will be determined by the controller 40 to indicate that the particular orifice is occluded or otherwise is in a state of bad health. Conversely, the presence of a drop ejected from a particular orifice when a drop is attempted to be ejected from that orifice, may be determined by the controller 40 to indicate that the particular orifice is not occluded or otherwise is in a state of good health. If a particular orifice is determined to be occluded or otherwise in bad health, controller 40 may control ejection of fluid 20 from one or more healthy orifices to compensate for the occlusion of the particular orifice. If more than a specified threshold number of orifices 18 are determined to be in bad health, controller 40 may notify the operator that drop ejection device 12 is not useful to dispense the required dispense volume and prompt the operator and use a different drop ejection device 12.

In another implementation the peak detector signal may be used to evaluate a real number of dispensed drops from simultaneously firing nozzles. The method enables high throughput and high precision.

FIG. 2 is a table 66 showing a correlation, at a particular total intended volume of 1,000 picoliters, between a particular drop volume 68, determined by or stored in controller 40, in picoliters of drops 38 from printhead 14, and the total number of drops 70 that should be ejected to ensure the intended total volume within an individual well 24a of wall tray 26. For example, a desired total intended volume in a well 24a of 1,000 picoliters is achieved by ejecting a total of forty drops 38 into well 24a from printhead 14 when the drop volume is 25 pL. The total of forty drops may be calculated to include drops that previously have been dispensed into well 24a, such as during a setup or calibration step such as orifice health determinations or drop volume determinations by controller 40. For this method, the drops ejected for the orifice health or drop volume determination would be counted as they are dispensed into a well 24a which is later intended to have a sufficiently large dispensed volume. The number of drops dispensed into this well during the orifice health or drop volume determination steps may be subtracted from the intended number of drops for well 24a to determine the correct number of drops remaining to be dispensed. After the correct number of drops required for each individual well 24a are determined, the dispensing into well tray 26 may proceed, including real time drop counting to dispense the exact number of drops required.

In this manner, a quick, efficient and accurate total number of drops 70 may be placed into multiple individual liquid receiving compartments 24 of a liquid receiving device on a large scale to achieve multiple intended total volumes. For example, minute and precise volumes of liquid 20 may be dispensed into the individual wells 24 of a well tray 26 that may include hundreds or thousands of individual wells 24, for example.

Advantages of the drop count determination of the process described herein include the lack of use of fluid additives to enable drop detection, improved accuracy and precision of dispensed volumes, the speed of the drop volume calculation method, and the lack of use of expensive detection hardware. Moreover, this method may be used "on-line" or in "real-time" during filling of a well tray, or before filling a well tray during a set-up or calibration routine.

The information contained in FIG. 2 is a very small sample shown for ease of illustration. In practice, much more information may be contained within the database or databases of controller 40 to allow the precise calculation of desired dispense volumes.

Figure 3:
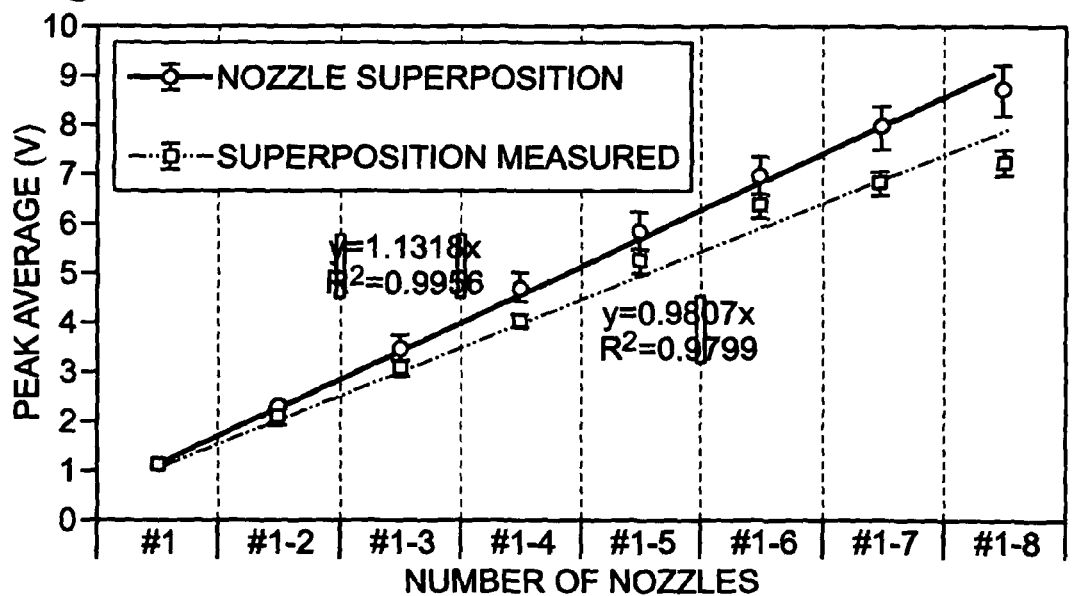
FIG. 3 is an exemplary plot showing dependency of signal strength versus number of simultaneously exposed drops.

FIG. 3 shows an exemplary plot showing dependency of signal strength versus number of simultaneously exposed drops.

Other variations and modifications of the concepts described herein may be utilized and fall within the scope of the claims below.

We claim:

1. A method of dispensing liquid, comprising:
attempting to eject drops from multiple orifices;
counting a number of said drops using a single detection device by:
illuminating said drops with a light source from a first direction;
detecting light refracted by said drops with a single detector placed at an angle with respect to said first direction;
calculating a dispensed volume of said drops from said counted number of drops;
determining that a first orifice which should have ejected one of said drops did not, wherein said first orifice is consequently designated as occluded; and
compensating for occlusion of said first orifice by ejecting more drops from a second orifice.

2. The method of claim 1, wherein said drops are ejected from said multiple orifices simultaneously.

3. The method of claim 2 wherein said counting said number of said drops using said single detection device further comprises:
generating a peak detection signal; and
evaluating a real number of said drops ejected from said multiple orifices.

4. The method of claim 3 wherein evaluating said real number of said drops ejected from said multiple orifices comprises applying a dependency between a peak signal strength and a number of simultaneously exposed drops; wherein said evaluating occurs in real time and at ejection frequencies up to 100,000 Hz.

5. The method of claim 2 wherein:
said ejecting comprises ejecting said drops into a specified well; and
said counting said number of said drops comprises counting said drops deposited in said specified well;
the method further comprising:
determining health of said at least one orifice; and
subtracting said number of said drops dispensed into said specified well from an intended number of drops for said specified well to determine a number of drops remaining to be dispensed into said specified well.

6. The method of claim 1 wherein said calculating comprises correlating said counted number of drops with a drop volume of each drop to determine said dispensed volume.

7. The method of claim 1 wherein counting said number of drops is conducted utilizing one of electrostatic detection, capacitive detection, acoustic drop detection, and optical detection.

8. The method of claim 1 wherein said light source comprises a laser, a light emitting diode, or an arc discharge lamp, and said single detector comprises a photo diode, a CMOS, a charge-coupled device, or a photo multiplying tube.

9. The method of claim 1 wherein said calculating of the dispensed volume is conducted during one of: (a) real time filling of a multiple-well liquid receptacle, and wherein the drops ejected during counting are subtracted from the total dispense volume for each well; and, (b) prior to real time filling of a receptacle.

10. The method of claim 1, further comprising positioning a liquid receiving device to receive an intended volume of said ejected drops, wherein said liquid receiving device comprises a biochemical testing device or a diagnostic strip device.

11. The method of claim 1 wherein said ejected drops comprises ejected drops including an absence of a light detection reagent added to said drops.

12. The method of claim 1 further comprising, when a threshold number of orifices become occluded, providing a notification to use a different drop ejection device.

13. A liquid dispensing device, comprising:
a single detection device positioned to receive drop information from ejected drops by a drop ejection device, in which the single detection device comprises:
a light source emitting light in a first direction; and
a single channel light detection device positioned at a non-zero angle relative to said first direction, wherein said single channel light detection device detects light from said light source scattered by said ejected drops; and
a controller that receives said drop information and uses said drop information to determine a number of said ejected drops,
said controller to determine when at least one of said drops is attempted to be ejected from a first orifice, but said first orifice did not eject at least one of said drops;
said controller to designate said first orifice as occluded when said controller determines said orifice did not eject at least one of said drops; and
said controller to compensate for occlusion of said first orifice by ejecting more drops from a second orifice.

* * * * *